United States Patent
Newman et al.

(10) Patent No.: US 9,052,305 B2
(45) Date of Patent: Jun. 9, 2015

(54) TEST STRIP DISPENSER

(75) Inventors: Michael John Newman, Ware (GB); Edwin Paul Earnshaw, Thriplow (GB); Yannick Pierre Hourmand, Haslingfield (GB); Andrew Macleod, Harston (GB); Benjamin Erland Impey, Haslingfield (GB); Barry Weber, Livermore, CA (US)

(73) Assignee: LifeScan, Inc., Wayne, PA (US)

( * ) Notice: Subject to any disclaimer, the term of this patent is extended or adjusted under 35 U.S.C. 154(b) by 1074 days.

(21) Appl. No.: 11/682,663

(22) Filed: Mar. 6, 2007

(65) Prior Publication Data

US 2008/0217354 A1 Sep. 11, 2008

(51) Int. Cl.
 *B65H 1/08* (2006.01)
 *G01N 33/487* (2006.01)
 *B65D 83/08* (2006.01)

(52) U.S. Cl.
 CPC ...... *G01N 33/48757* (2013.01); *B65D 83/0829* (2013.01)

(58) Field of Classification Search
 USPC ............ 221/50, 65, 175, 176, 178, 191, 197, 221/198, 208–210, 214, 216, 224, 226–229, 221/233–235, 246–249, 259, 261, 263, 267, 221/279, 280, 287, 303
 See application file for complete search history.

(56) References Cited

U.S. PATENT DOCUMENTS

| | | | | |
|---|---|---|---|---|
| 788,730 | A * | 5/1905 | Rogers | 221/246 |
| 914,040 | A * | 3/1909 | Haines | 221/229 |
| 1,756,439 | A * | 4/1930 | Schick | 30/536 |
| 2,288,870 | A * | 7/1942 | Ernest et al. | 221/187 |
| 3,563,412 | A * | 2/1971 | James | 221/224 |
| 4,872,593 | A * | 10/1989 | Behringer | 221/231 |
| 5,337,897 | A * | 8/1994 | Yablans | 206/581 |
| 5,383,569 | A * | 1/1995 | Muto | 221/203 |
| 5,505,308 | A | 4/1996 | Eikmeier et al. | |
| 6,176,119 | B1 | 1/2001 | Kintzig | |
| 6,378,702 | B1 | 4/2002 | Kintzig | |
| 6,908,008 | B2 * | 6/2005 | Pugh | 221/135 |
| 6,997,343 | B2 | 2/2006 | May et al. | |
| 7,138,089 | B2 * | 11/2006 | Aitken et al. | 422/82.01 |
| 2002/0162849 | A1 * | 11/2002 | Chen | 221/65 |
| 2003/0002387 | A1 | 1/2003 | Bottwein et al. | |
| 2003/0212345 | A1 | 11/2003 | McAllister et al. | |
| 2004/0178216 | A1 | 9/2004 | Brickwood et al. | |
| 2005/0186162 | A1 | 8/2005 | Sato | |
| 2005/0281706 | A1 * | 12/2005 | Funke et al. | 422/63 |
| 2006/0118570 | A1 | 6/2006 | Fowler et al. | |
| 2006/0182656 | A1 | 8/2006 | Funke et al. | |
| 2006/0266765 | A1 | 11/2006 | Pugh | |
| 2008/0094804 | A1 * | 4/2008 | Reynolds et al. | 361/727 |

FOREIGN PATENT DOCUMENTS

| | | |
|---|---|---|
| EP | 1 321 769 A | 6/2003 |
| EP | 1 362 551 A | 11/2003 |
| EP | 1 726 950 A | 11/2006 |
| JP | 2002-116214 A | 4/2002 |
| JP | 2004-113771 A | 4/2004 |
| WO | WO 2006047135 A1 | 5/2006 |

* cited by examiner

*Primary Examiner* — Gene Crawford
*Assistant Examiner* — Kelvin L Randall, Jr.

(57) ABSTRACT

In one aspect, a method of dispensing a test strip is provided in which the dispensed test strip remains stationary while the inner housing moves within an outer housing. In another embodiment, a test strip dispenser is provided that dispenses one test strip at a time. The test strip dispenser includes a movable inner housing nested inside an outer housing. A test strip dispensing system is also described.

16 Claims, 12 Drawing Sheets

TEST STRIP DISPENSER

Apparatuses and methods for measuring components of biological fluids as well as test strips for use in such devices are well known. Typically, the test strips are stored in a disposable container that is separate from the apparatus that measures the fluid component of interest. In the known test strip system, a test strip is removed from the container, a fluid sample is dispensed onto the strip, and the strip is inserted into a photometric or electrochemical meter for analysis of the desired component. After analysis is completed, the test strip is extracted from the meter and the strip is discarded.

Ease of use of hand held test strip dispensers and meters is important, particularly for those dispensers that will be used by persons with diminished hand-eye coordination or finger sensation. For example, persons with diabetes typically have either or both impaired vision and diminished fingertip sensation. Such persons must use test strips and meters to test their blood glucose levels a number of times a day. However, the typical test strip is only several millimeters in width and length and, thus, difficult to manipulate. Additionally, conventional strips are typically packed in small, cylindrical containers from which it is difficult to easily extract a single strip Accordingly, applicants heretofore provide for an invention that ameliorates the drawbacks of the known test strip and associated components discussed above. In one aspect a test strip dispenser is provided that dispenses one test strip at a time. The test strip dispenser includes an interior volume to store a plurality of test strips, an aperture through which a test strip is dispensed and a groove. The test strip dispenser further includes a biasing device that disposes the inner housing in a first direction and an outer housing. In this embodiment, the outer housing includes an opening in substantial alignment with the aperture of the inner housing to allow for passage of the test strip. The outer housing further includes a guide member that mates with the groove of the inner housing so that the test strip remains stationary when the inner housing is moved along the guide member of the outer housing in a direction generally opposite the first direction.

In yet another embodiment, a system is provided that delivers a test strip to a testing position. The system includes a plurality of test strips stored inside a test strip dispenser and a meter. The test strip dispenser includes an interior volume to store a plurality of test strips, an aperture through which a test strip is dispensed and a groove. The test strip dispenser further includes a biasing device that disposes the inner housing in a first direction and an outer housing. In this embodiment, the outer housing includes an opening in substantial alignment with the aperture of the inner housing to allow for passage of the test strip. The outer housing further includes a guide member that mates with the groove of the inner housing so that the test strip remains stationary when the inner housing is moved along the guide member of the outer housing in a direction generally opposite the first direction. The meter includes a strip port configured to engage the inner housing of the test strip dispenser so that the inner housing moves along the guide member while a strip port connector within the meter engages the test strip.

These and other embodiments, features and advantages will become apparent to those skilled in the art when taken with reference to the following more detailed description of the invention in conjunction with the accompanying drawings that are first briefly described herebelow.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), of which.

DETAILED DESCRIPTION

Various exemplary embodiments disclosed herein includes test strip dispensing methods and devices suited for storage or delivery of a wide variety of electrochemical test strips and photometric test strips, such as test strips suitable for use in the determination of analytes in whole blood or derivatives thereof. In one aspect, the test strip can store a plurality of such test strips and can dispense individual test strips for receipt by a diagnostic device known as in the art as a "meter." Also disclosed herein are test strip dispensing systems that include a meter configured to mate with the test strip dispenser and to receive test strips therefrom.

It is noted that the following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

FIGS. 1A-1C and FIGS. 2-4 illustrate a test strip dispenser 100 according to an exemplary embodiment. Test strip dispenser 100 includes a proximal end 102, a distal end 104, an outer housing 106 and an inner housing 108. Inner housing 108, which is configured to house a plurality of test strips 200 (e.g., a stack of test strips), is nested inside outer housing 106 and is moveable therein. Outer housing 106 and inner housing 108 are generally rectangular in shape and may be formed of a suitable material, preferably such as, for example, acrylonitrile butadiene styrene, polycarbonate or combinations thereof.

Each of the plurality of test strips 200 that can be used with various embodiments described and illustrated herein are generally elongate in shape and are sized to fit within inner housing. In the illustrated embodiment, test strip 200 can be, for example, a OneTouch® Ultra® brand glucose test strip or other suitable test strips that are commercially available.

Each of the plurality of test strips 200 is usually stored in test strip dispenser 100 with the distal end on which a fluid sample is applied extending toward distal end of test strip dispenser 100 and, for electrochemical type test strips, with the proximal end containing electrical connections extending toward proximal end of the test strip dispenser 100. This ensures that when a single test strip is removed from test strip dispenser 100 by a meter, the test strip will be in a correct orientation for applying the fluid sample and, for electrochemical type test strips, for making an electrical connection with the meter.

Figure 1A:
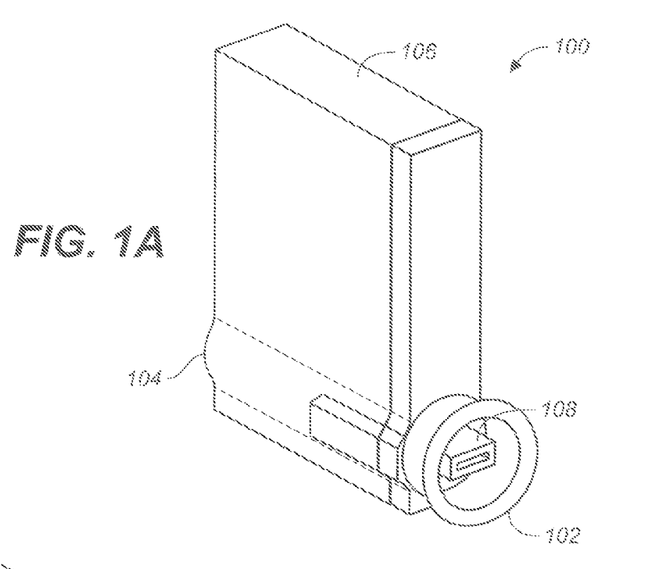
FIGS. 1A, 1B and 1C are perspective, exploded and partially exploded views, respectively, of a test strip dispenser according to an exemplary embodiment.
Figure 1B:
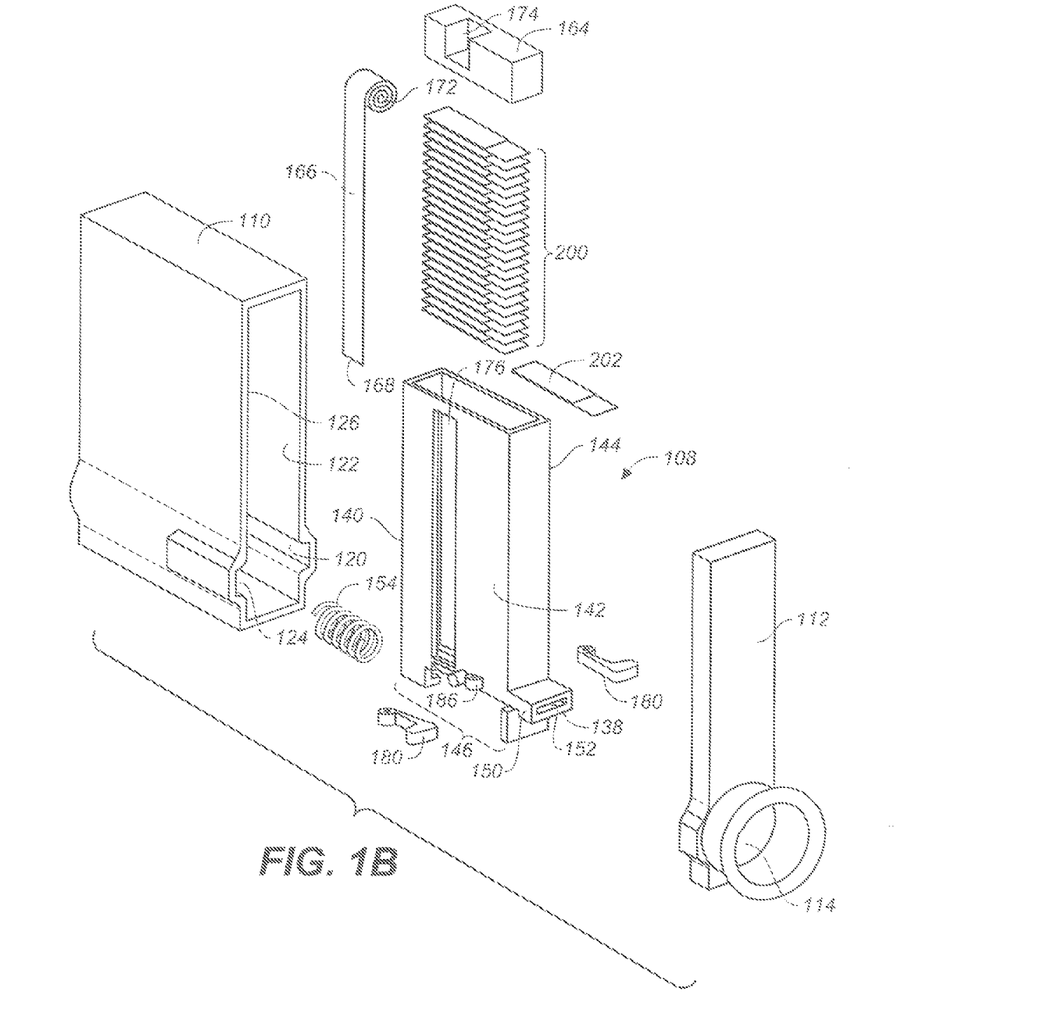
Figure 1C:
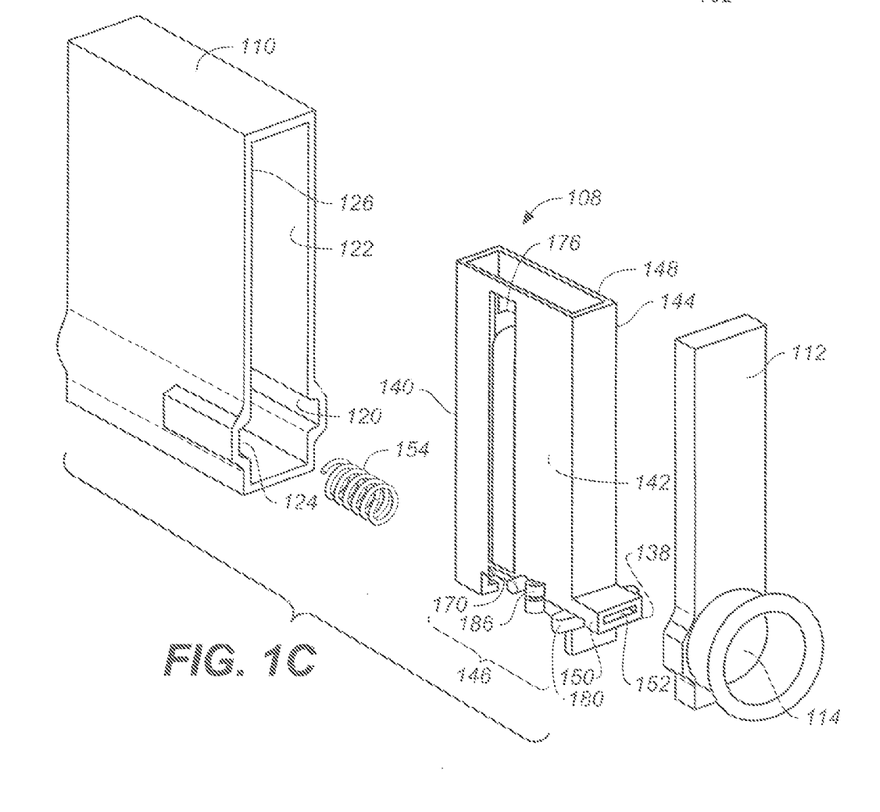

Referring to FIGS. 1A-1C, outer housing 106 includes a first member 110 and a second member 112. Second member 112 includes an opening 114 for gaining access to test strip 200 stored in an inner housing 108. First member 110 and second member 112 are joined together by, for example, a snap fit or ultrasonic welding to form a space for holding inner housing therein.

Figure 2:
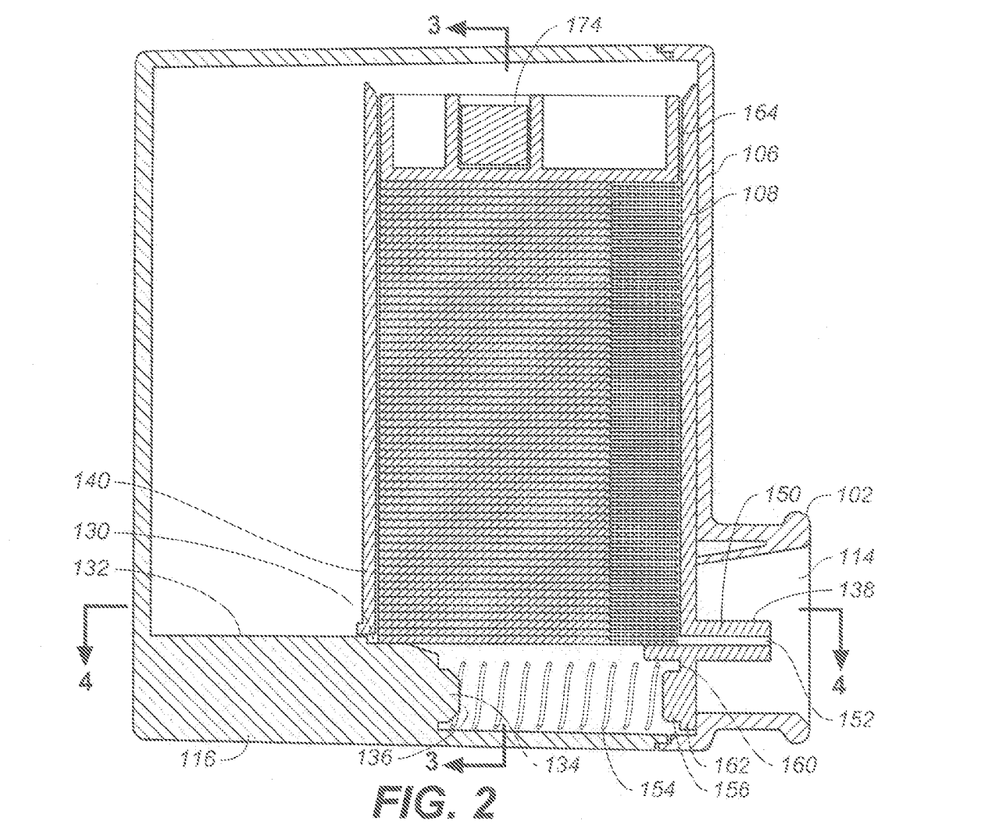
FIGS. 2, 3 and 4 are cross-sectional views of the test strip dispenser illustrated in FIG. 1A.
Figure 5:
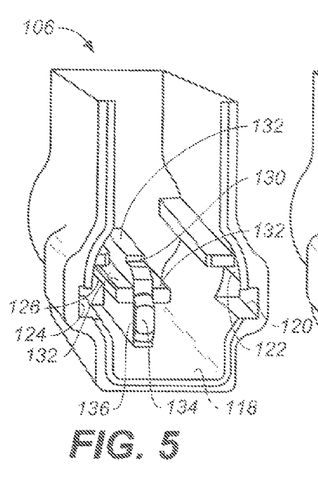
FIG. 5 is a perspective partial cross-sectional view of the outer housing of the test strip dispenser shown in FIGS. 1A-1C.
Figure 6:
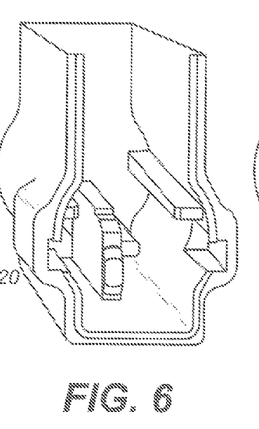
FIGS. 6 and 7 are perspective partial cross-sectional views of the outer housing of a test strip dispenser according to other exemplary embodiments.
Figure 7:
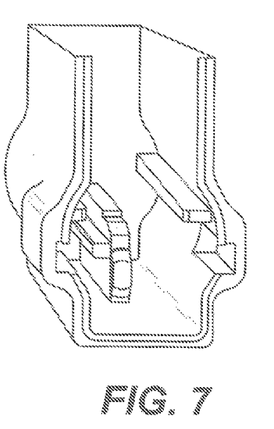

As illustrated in FIGS. 2 and 5, outer housing 106 further includes a guide member 116 on a first inner surface 118, a first recess 120 on a second inner surface 122 and an optional second recess 124 on a third inner surface 126. Guide member 116 includes a ledge 128 and a stop 130 on a proximal end 136 and a surface 132 on which inner housing 108 moves. Guide member 116 optionally includes a first spring locator 134 on proximal end 136. In one embodiment illustrated in FIG. 5, the cross section of guide member 116 is t-shaped. In other embodiments shown in FIGS. 6 and 7, guide member 116 may be a modified to shape in which a left or right arm, respectively, is removed.

Referring to FIGS. 1B, 1C and 2, inner housing 108 includes a proximal end 138, a distal end 140, a first side 142, a second side 144, a first end 146 and a second end 148. Proximal end 138 of inner housing 108 includes a projection 150 with an aperture 152 through which a test strip travels during dispensing. Projection 150 is oblong in shape and is configured to fit within opening 114 in outer housing 106.

Figure 12:
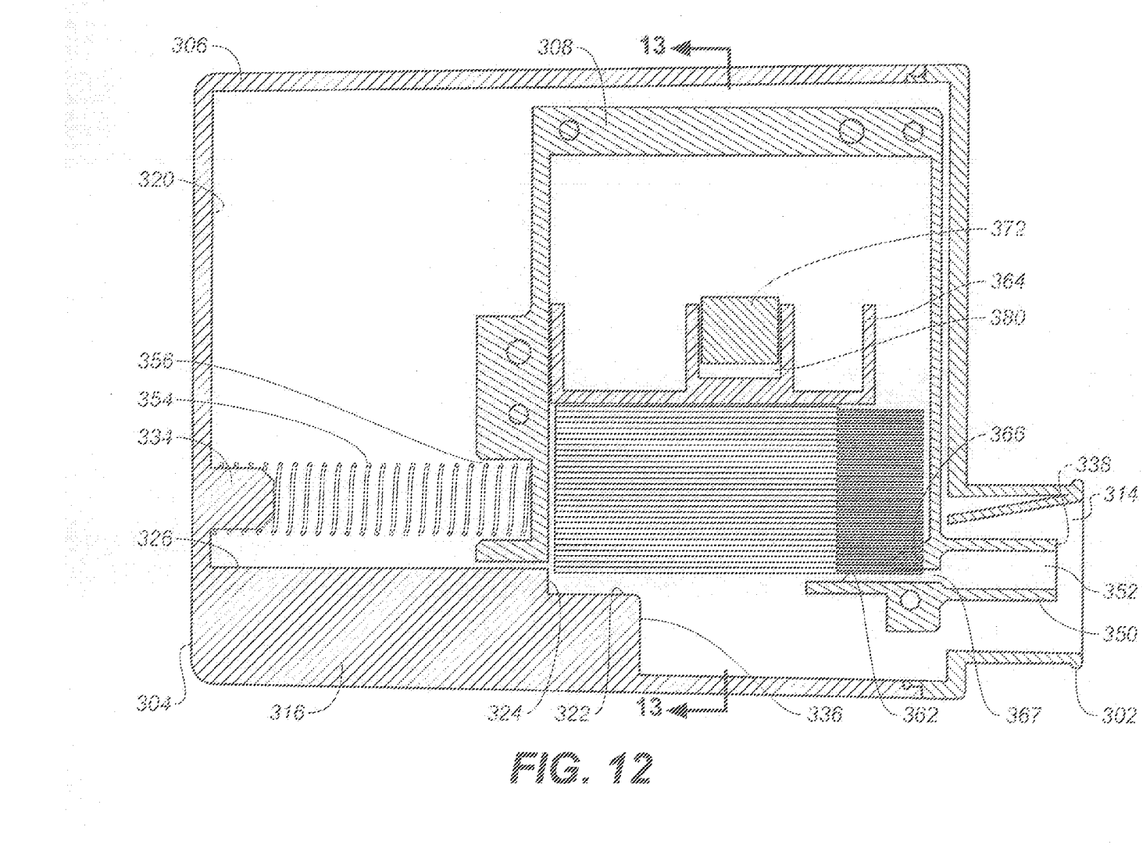
FIGS. 12 and 13 are cross-sectional views of the test strip dispenser shown in FIGS. 11A-11C.

Inner housing 108 is biased toward proximal end 102 of test strip dispenser 100 by a spring 154. Spring 154 may be located proximal to guide member 116, as shown in FIG. 2, or may be located distal to proximal end 138 of inner housing 108 as illustrated in FIG. 12. Having spring 154 located proximal to guide member 116 results in a more compact test strip dispenser 100. When spring 154 is located proximal to guide member 116, a second spring locator 156 is optionally located on a first side 160 of a protrusion 162 on first end 146 of inner housing 108 (see FIGS. 2 and 8A).

Figures 8A, 8B:
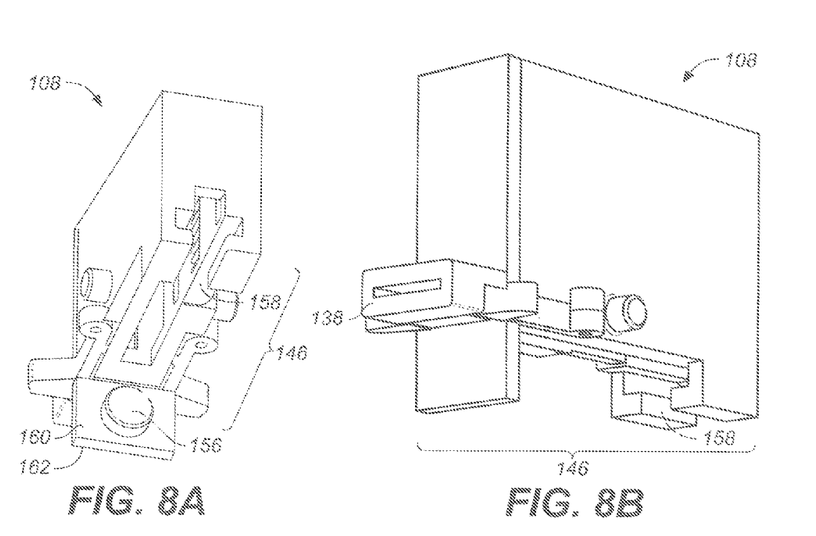
FIG. 8A is a perspective close up view of the first end of the inner housing of the test strip dispenser shown in FIGS. 1A-1C.
FIG. 8B is a perspective close up view of the proximal end of the inner housing of the test strip dispenser shown in FIGS. 1A-1C.

As illustrated in FIGS. 8A and 8B, inner housing 108 further includes a groove 158 at first end 146 that mates with and moves on guide member 116 on first inner surface 118 of outer housing 106 during test strip dispensing, as will be described in more detail with reference to FIGS. 9A-9D. In one embodiment shown in FIGS. 8A and 8B, groove 158 is t-shaped and spans about one fourth of the distance from distal end 140 to proximal end 138 of inner housing 108. Although groove 158 is illustrated as having a "T" cross-section, groove 158 may be of any shape compatible with the shape of guide member 116 as long as the groove 158 mates and moves on guide member 116.

Figure 3:
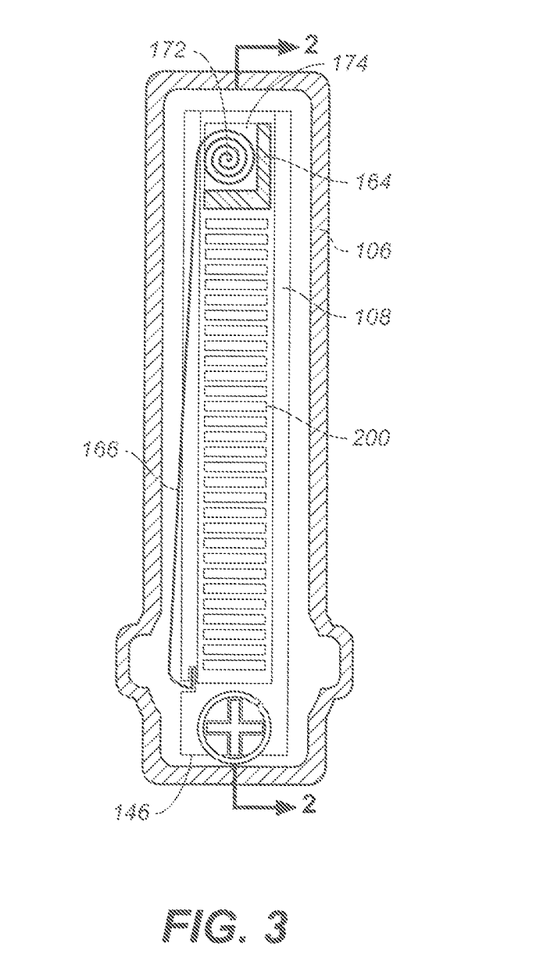

As illustrated in FIGS. 1B, 2 and 3, a spring-loaded platform 164 biases plurality of strips 200 toward first end 146 of inner housing 108. An example spring used to bias platform 164 is a spiral spring 166. A first end 168 of spiral spring 166 may be held in place in a slot 170 near first end 146 of inner housing 108 (see FIG. 1B). Alternatively, first end 168 of spiral spring 166 may be coupled near first end 146 of inner housing 108 by a suitable process such as, for example, plastic welding, bonding, or preferably heat staking. A second end 172 of spiral spring 166 forms a spiral that resides in a niche 174 in platform 164. To accommodate a suitable fit of plurality of test strips 200 within inner housing 108, spiral spring 166 may optionally extend through a longitudinal space 176 in first side 146 of inner housing 108.

Figure 4:
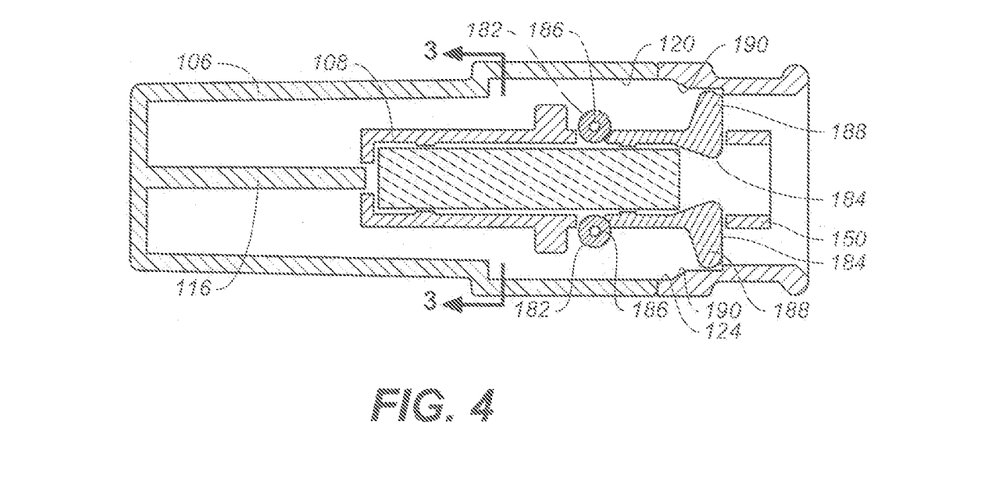

Inner housing 108 further includes an anti-jamming mechanism having at least one flipper 180 with a first end 182 and a second end 184, as illustrated in FIG. 4. First end 182 of at least one flipper 180 is pivotally attached to first side 142 of inner housing 108 with, for example, a hinge 186. Second end 184 of at least one flipper 180 includes an arm 188 that engages a sloping surface 190 of first recess 120 of outer housing 106 if a test strip is not engaged by a meter during test strip dispensing, as will be described with reference to FIG. 10C.

Referring to FIGS. 9A-9D and 10A-10C together, a sequence of steps in a method for dispensing a test strip is illustrated. The provision of an exemplary test strip dispenser that may be used with the subject method is depicted in FIGS. 1A-1C, 2-4 and 8A-8B in which like elements of the test strip dispenser of the earlier figures are identified with like numerals.

Figure 9A:
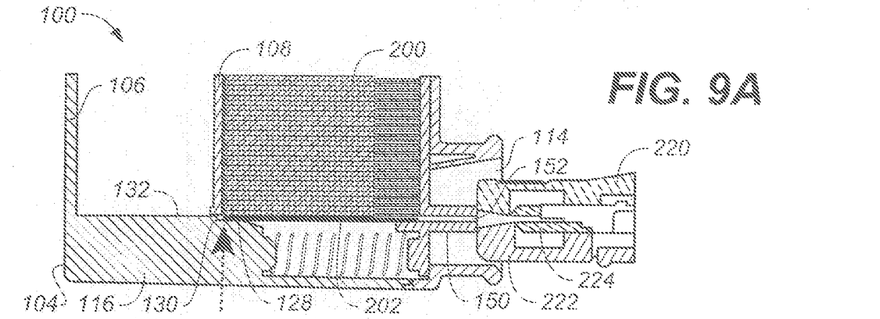
FIGS. 9A-9D are schematic partial cross-sectional side views of a sequence of steps used in a process for dispensing a test strip from a test strip dispenser to a test position in a meter.
Figure 10A:
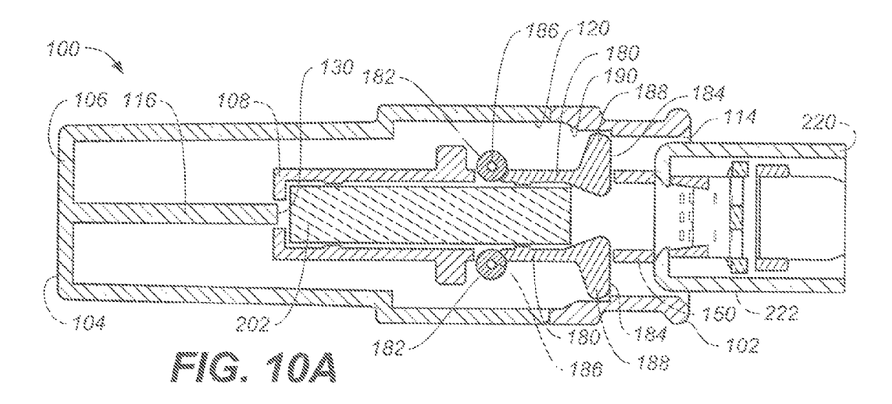
FIGS. 10A-10C are schematic cross-sectional top views of a sequence of steps used in an anti-jamming process.

In the first step of the subject method, test strip dispenser 100 housing plurality of test strips 200 and a meter 220 are provided according to exemplary embodiments (see FIGS. 9A and 10A). Prior to a first test strip 202 being dispensed, test strip dispenser 100 is in a rest position in which groove 158 of inner housing 108 rests on surface 132 of guide member 116 and plurality of test strips 200 rests on ledge 128 of guide member 116.

Figure 9B:
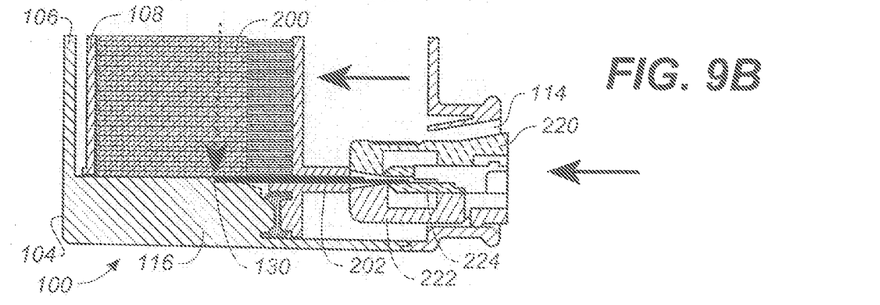
Figure 10B:
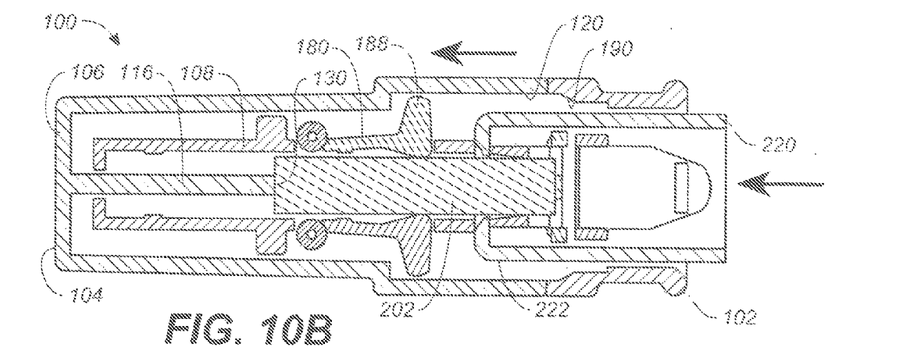
Figure 10C:
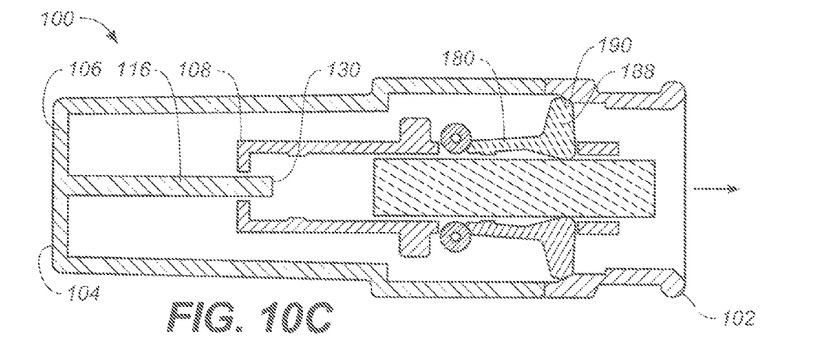

As illustrated in FIGS. 9B and 10B, a strip port 222 of meter 220 is then inserted into opening 114 of outer housing 106 and strip port 222 engages with projection 150 of inner housing 108, urging inner housing 108 toward distal end 104 of test strip dispenser 100 along guide member 116. While inner housing 108 is urged along guide member 116, first test strip 202 remains substantially stationary while the remaining plurality of test strips 200 moves toward distal end 104 of test strip dispenser 100. As inner housing 108 is urged along guide member 116, the proximal end of first test strip 202 engages incline of second end 184 of at least one flipper 180, pushing at least one flipper 180 laterally outward and toward the inner walls of outer housing 106. Inner housing 108 continues to be urged along guide member 116 until it is pushed toward distal end 104 of test strip dispenser 100 as far as possible, at which time the distal end of first test strip 202 is engaged with stop 130 of guide member 116 and the proximal end of first test strip 202 is engaged with a strip port connector 224 of meter 220, as illustrated in FIGS. 9B and 10B. It should be noted that the height of stop 130 is usually slightly smaller than the thickness of the test strip so that only one test strip at a time is engaged with stop 130. At this point, arm 188 on second end 184 of the at least one flipper 180 moves freely within first recess 120 of outer housing 106.

Figure 9C:
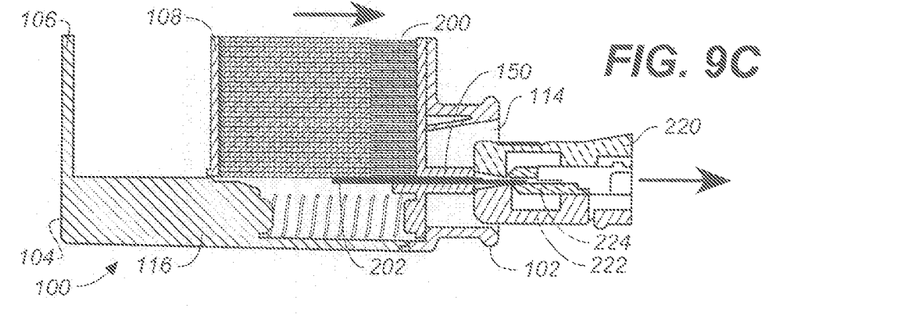

As strip port 222 is removed from opening 114 of outer housing 106 with first test strip 202 engaged in strip port connector 224, first test strip 202 is pulled through aperture 152 in projection 150 of inner housing 108, and inner housing 108 is biased toward proximal end 102 of test strip dispenser 100 (see FIG. 9C). It should be noted that aperture 152 is sized to accommodate only one test strip at a time. As soon as the distal end of first test strip 202 enters aperture 152, a second test strip is biased by platform toward first end 146 of inner housing 108 into a dispensing position (not shown). If strip port connector 224 does not engage with first test strip 202, arm 188 of at least one flipper 180 engages with sloping surface 190 in first recess 120 of outer housing 106, preventing inner housing 108 from moving back to the rest position and preventing the distal end of a second test strip from engaging with stop 130 of guide member 116 (see FIG. 10C). Inner housing 108 remains locked in this anti-jamming position until the meter is urged against inner housing 108 again and strip port connector 224 engages first test strip 202.

Figure 9D:
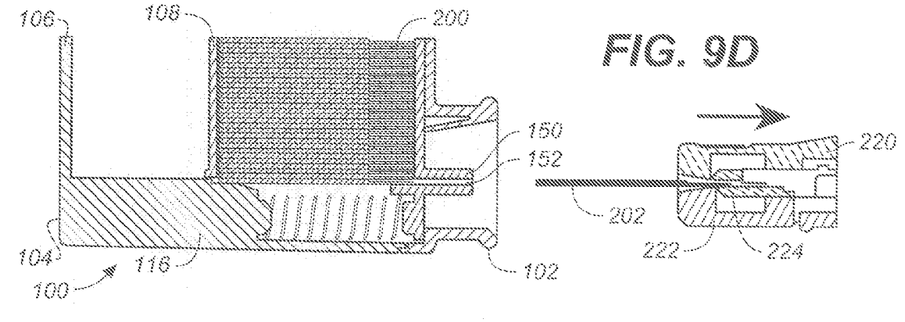

As illustrated in FIG. 9D, first test strip 202 is completely removed from test strip dispenser 100 while remaining engaged in strip port connector 224 of meter 220 and is positioned for testing.

FIGS. 11A-11C and FIGS. 12-16 illustrate a test strip dispenser 300 according to another exemplary embodiment. Test strip dispenser 300 includes a proximal end 302, a distal end 304, an outer housing 306 and an inner housing 308. Inner housing 308, which is configured to house a plurality of test strips 400 (e.g., a stack of test strips), is nested inside outer housing 306 and is moveable therein. Outer housing 306 and inner housing 308 are generally rectangular in shape and may be formed of a suitable material, preferably such as acrylonitrile butadiene styrene, polycarbonate or combinations thereof.

Each of the plurality of test strips 400 that can be used with various embodiments described and illustrated herein are generally elongate in shape and are sized to fit within the inner housing. In the illustrated embodiment, test strip 400 can be, for example, a glucose test strip as shown and described in U.S. Pat. No. 6,749,887, which is hereby incorporated in full by reference. Alternatively, the other suitable commercially available test strips may also be used with various embodiments described and illustrated herein.

Each of the plurality of test strips 400 is usually stored in test strip dispenser 300 with the distal end on which a fluid sample is applied extending toward distal end 304 of test strip dispenser 300 and, for electrochemical type test strips, with the proximal end containing electrical connections extending toward proximal end 302 of test strip dispenser 300. This ensures that when a single test strip is removed from test strip dispenser 300 by a meter, the test strip will be in a correct orientation for applying the fluid sample and, for electrochemical type test strips, for making an electrical connection with the meter.

Figure 11A:
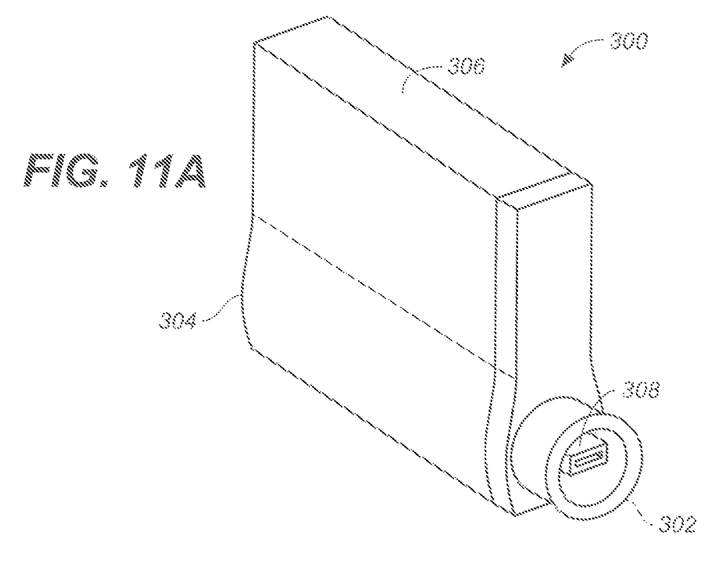
FIGS. 11A-11C are perspective, exploded and partially exploded views, respectively, of a test strip dispenser.
Figure 11B:
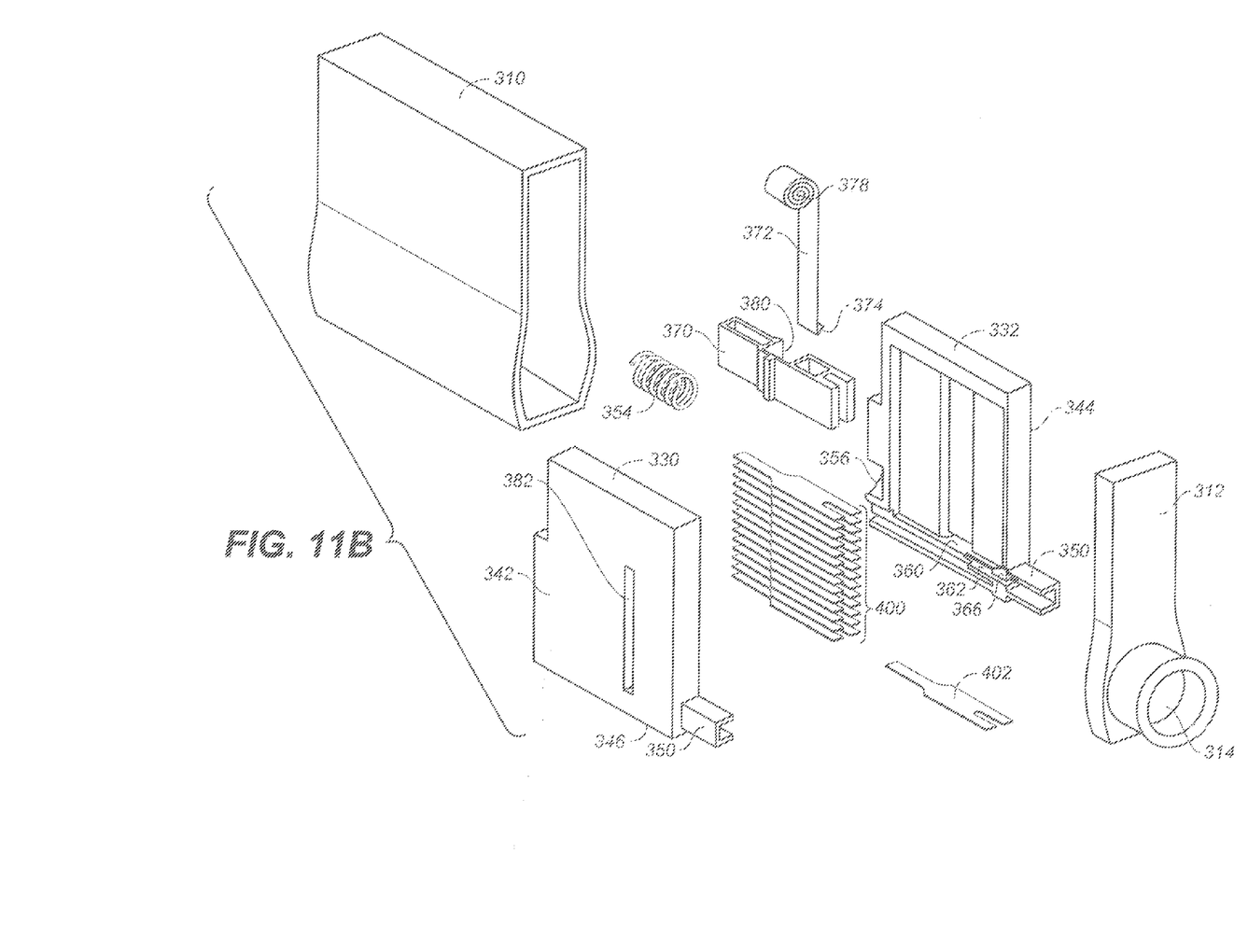
Figure 11C:
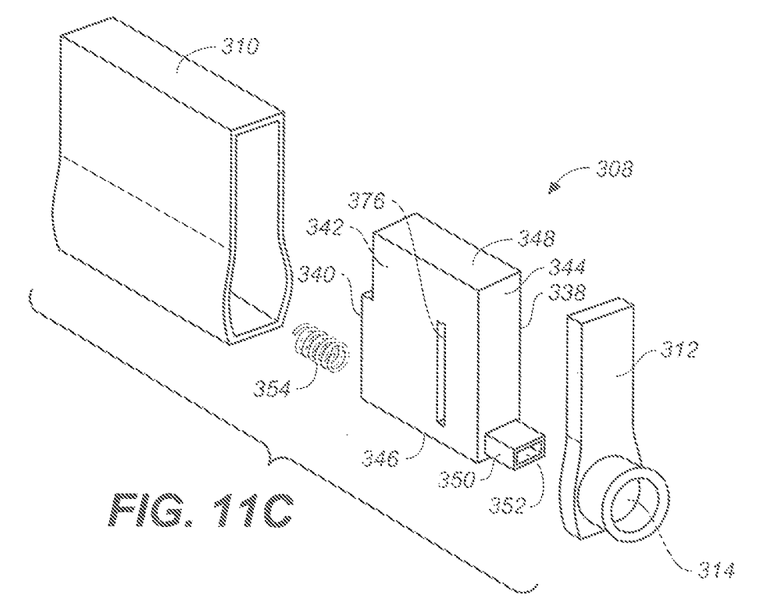
Figure 13:
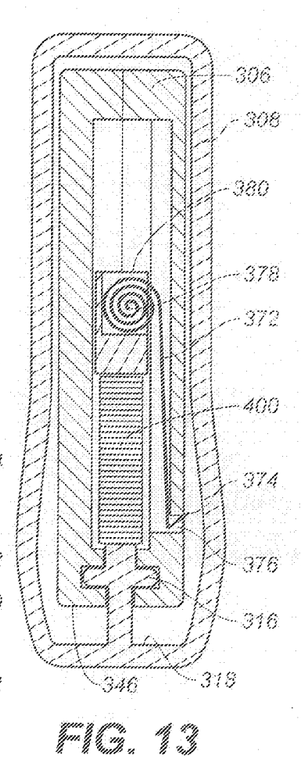
Figure 14:
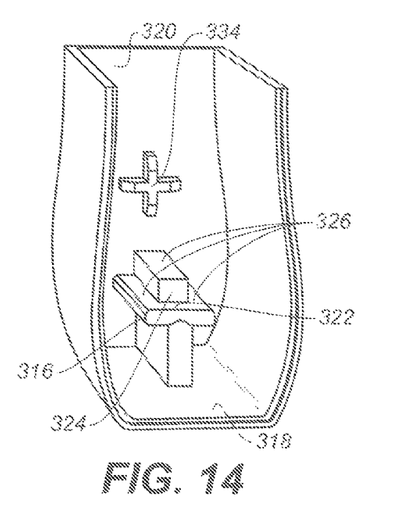
FIG. 14 is a perspective, partial cross-sectional view of the outer housing of the test strip dispenser shown in FIGS. 11A-11C.

Referring to FIGS. 11A-11C, outer housing 306 includes a first member 310 and a second member 312 with an opening 314 for gaining access to a test strip stored in inner housing 308. First member 310 and second member 312 are joined together by, for example, ultrasonic welding or a snap fit to form a space for holding inner housing 308 therein. As illustrated in FIGS. 12-14, outer housing 306 further includes a guide member 316 on a first inner surface 318 and an optional spring locator 334 on a second inner surface 320. In one embodiment, guide member 316 is t-shaped and includes a ledge 322, a stop 324 on a proximal end 336 and a surface 326 on which inner housing 308 moves. In other embodiments, guide member 316 may be a modified t shape in which a left or right arm, respectively, is removed (not shown).

Referring again to FIGS. 11B-11C, inner housing 308 includes a first portion 330 and a second portion 332 joined together by, for example, screws or ultrasonic welding to form a cavity configured to house plurality of test strips 400. Inner housing 308 may also be formed of a single molded body. As shown in FIG. 11C, in assembled form, inner housing includes a proximal end 338, a distal end 340, a first side 342, a second side 344, a first end 346 and a second end 348. Proximal end 338 of inner housing 308 includes a projection 350 with an aperture 352 through which a test strip travels during dispensing. Projection 350 is oblong in shape and is configured to fit within opening 314 in outer housing 306.

Inner housing 308 is biased toward proximal end 302 of test strip dispenser 300 by a spring 354. Spring 354 is located distal to proximal end 338 of inner housing 308 as illustrated in FIG. 12. Inner housing 308 may optionally include a recess 356 on distal end 340 for locating an end of spring 354 (see FIGS. 12 and 15).

Figure 15:
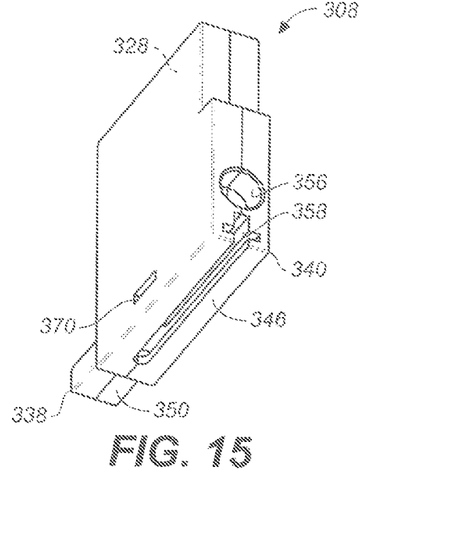
FIG. 15 is a perspective view of the first end of the inner housing of the test strip dispenser shown in FIGS. 11A-11C.

As illustrated in FIG. 15, inner housing 308 further includes a groove 358 at first end 346 that mates with and moves on guide member 316 on first inner surface 318 of outer housing 306 during test strip dispensing, as will be described in more detail with reference to FIGS. 17A-17D. In one embodiment illustrated in FIG. 15, groove 358 may be t-shaped and spans the length of first end 346 of inner housing 308. Alternatively, the groove 358 may be any shape compatible with the shape of guide member 316.

Figure 16:
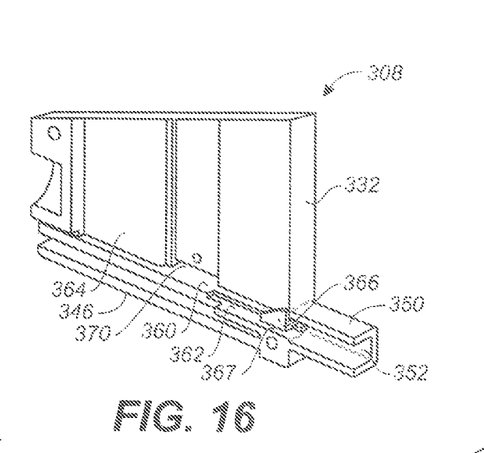
FIG. 16 is a close up perspective view of the inner surface of the second portion of the inner housing shown in FIG. 11B.

As illustrated in FIG. 16, inner housing 308 further includes a first shelf 360 on which plurality of test strips 400 rests before and during test strip dispensing and a second shelf 362 on a first inner surface 364 in which a test strip being dispensed drops during test strip dispensing. Additionally, inner housing 308 includes an arm 366 projecting from a second inner surface 368 near proximal end 338 of inner housing 308 that engages the plurality of test strips 400 not being dispensed during the dispensing process, as will be described below. Arm 366 also forms one side of a channel 367 through which only one test strip at a time can move. The other side of channel 367 is formed by second shelf 362.

Referring again to FIGS. 11B, 12 and 13, a spring-loaded platform 370 biases plurality of strips 400 toward first end 346 of inner housing 308. An example spring used to bias platform is a spiral spring 372. A first end 374 of spiral spring 372 may be held in place in a slot 376 near first end 346 of inner housing 308. Alternatively, first end 374 of spiral spring 372 may be affixed near first end 346 of inner housing 108 by a process such as heat staking. A second end 378 of spiral spring 372 forms a spiral that resides in a niche 380 in platform 370. To accommodate a snug fit of plurality of test strips 400 within inner housing 308, spiral spring 372 may optionally extend through a longitudinal space (not shown) in first side 346 of inner housing 308.

Inner housing 308 may optionally include a window 382 in first side 342 or second side 344 for viewing the number of test strips remaining in inner housing 308 (see FIG. 11B). Alternatively, both the inner and outer housings may be formed of a generally transparent material or even a translucent material to allow for visualization of the number of test strips remaining in the dispenser.

Referring to FIGS. 17A-17D and FIG. 18 together, a sequence of steps in a method for dispensing a test strip. The provision of an exemplary test strip dispenser that may be used with the subject method is depicted in FIGS. 11A-11C and 12-16 in which like elements of the test strip dispenser of the earlier figures are identified with like numerals.

Figure 17A:
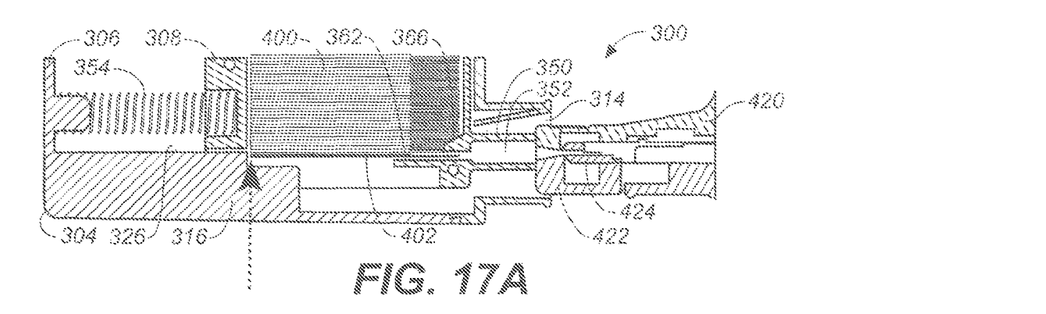
FIGS. 17A-17D are schematic partial cross-sectional side views of a sequence of steps used in a process for dispensing a test strip from a test strip dispenser to a test position.

In the first step of the subject method, test strip dispenser 300 housing plurality of test strips 400 and a meter 420 are provided according to exemplary embodiments (see FIG. 17A). Prior to a first test strip 402 being dispensed, test strip dispenser 300 is in a rest position in which a portion of groove 358 of inner housing 308 rests on surface 326 of guide member 316 and plurality of test strips 400 rests on first shelf 360 in first inner surface 364 of inner housing 308 (see FIG. 18 for first shelf 360).

Figure 17B:
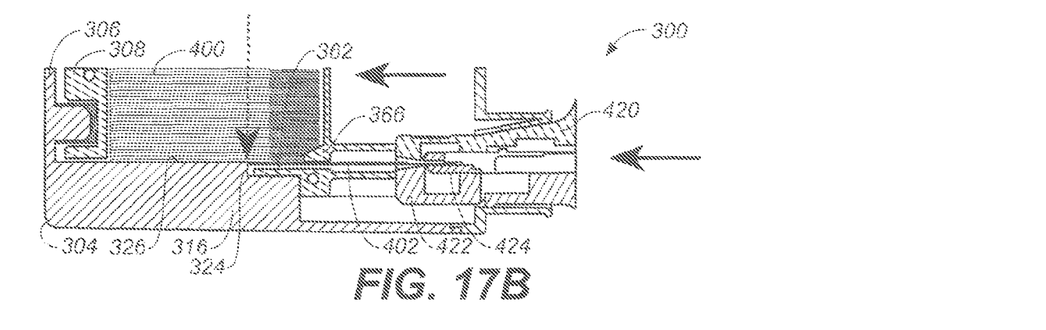

As illustrated in FIG. 17B, a strip port 422 of meter 420 is then inserted into opening 314 of outer housing 306 and strip port 422 engages with projection 350 of inner housing 308, urging inner housing 308 toward distal end 304 of test strip dispenser 300 along guide member 316. While inner housing 308 is urged along guide member 316, arm 366 projecting from second inner surface 368 of inner housing 308 engages all of the plurality of test strips 400 except first test strip 402. At this step, first test strip 402 remains substantially stationary while the remaining plurality of test strips 400 moves toward distal end 304 of test strip dispenser 300. Inner housing 308 continues to be urged along guide member 316 until it is pushed toward distal end 304 of test strip dispenser 300 as far as possible, at which time first test strip 402 drops onto second shelf 362 on first inner surface 364 of inner housing 308 and the distal end of first test strip 402 is engaged with stop 324 of guide member 316 (see FIGS. 17B and 18). At or near the same time the distal end of first test strip 402 is engaged with stop 324 of guide member 316, the proximal end of first test strip 402 is engaged with a strip port connector 424 of meter 420. First test strip 402 drops onto second shelf 362 to release pressure on the remaining plurality of test strips 400 moving toward distal end 304 of test strip dispenser 300 and to lessen the retention force required by strip port connector 424.

Figure 17C:
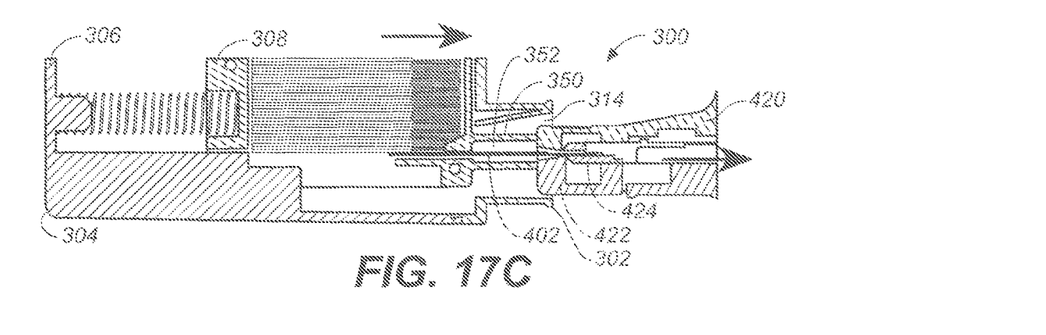

Referring to FIG. 17C, as strip port 422 of meter 420 is removed from opening 314 of outer housing 306 with first test strip 402 engaged in strip port connector 424, first test strip 402 is pulled through channel 367 and then is pulled through aperture 352 in projection 350 of inner housing 308. As first test is pulled through channel 367 and aperture 352, inner housing 308 is biased toward proximal end 302 of test strip dispenser 300.

Figure 17D:
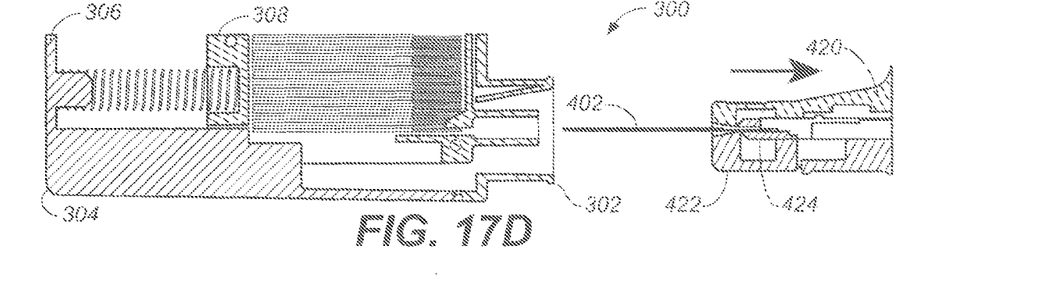
Figure 18:
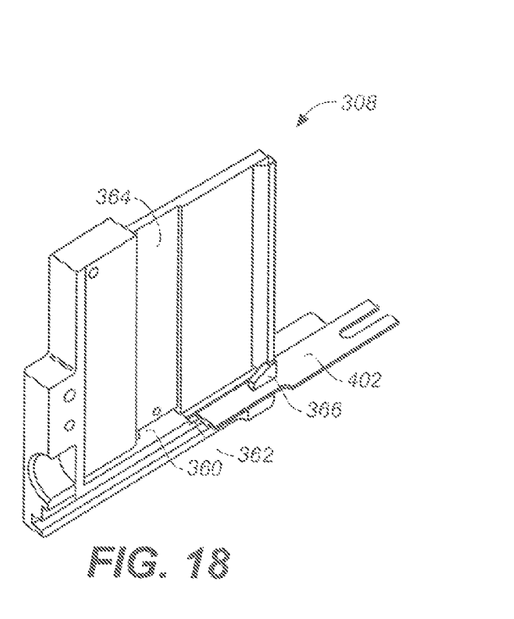
FIG. 18 is a close up perspective view of the inner surface of the second portion of the inner housing shown in FIG. 11B illustrating the location of a test strip being dispensed during a test strip dispensing process.

As illustrated in FIG. 17D, first test strip 402 is completely removed from test strip dispenser 300 while remaining engaged in strip port connector 424 of meter 420 and is positioned for testing.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed is:

1. A test strip dispenser, comprising
   an inner housing within an outer housing and moveable in the outer housing along a guide member of the outer housing, the inner housing having an interior volume to store a plurality of test strips including a test strip to be dispensed, the inner housing having an aperture through which the test strip to be dispensed is dispensed, the inner housing including a groove;
   a device that biases the inner housing in a first direction; and
   the outer housing having an opening in substantial alignment with the aperture of the inner housing to allow for passage of the test strip, the outer housing guide member having a first end, a second end, a length between the first and second ends and a stop at one end for engagement with an end of the test strip, wherein the guide member mates with the groove of the inner housing so that the test strip to be dispensed remains stationary when the inner housing and the remaining plurality of test strips are moved along the guide member of the outer housing in a direction generally opposite the first direction.

2. The test strip dispenser of claim 1, wherein the groove comprises a T-shaped cross-section.

3. The test strip dispenser of claim 1, wherein the groove is located on a first end of the inner housing.

4. The test strip dispenser of claim 1, wherein the guide member comprises a T-shaped rail.

5. The test strip dispenser of claim 1, wherein the guide member is located on a first inner surface of the outer housing.

6. The test strip dispenser of claim 1, wherein the inner housing further comprises a channel near the aperture through which the test strip is dispensed and the channel is configured to accommodate one test strip at a time.

7. The test strip dispenser of claim 1, further comprising a cap on the opening of the outer housing.

8. The test strip dispenser of claim 1, further comprising a spring-loaded platform within the inner housing that biases the plurality of test strips toward the proximal end of the inner housing.

9. The test strip dispenser of claim 1, wherein the inner housing is comprised of a first portion joined to a second portion.

10. The test strip dispenser of claim 1, wherein the outer housing is comprised of a first member joined to a second member.

11. The test strip dispenser of claim 1, wherein the biasing device comprises a spring.

12. The test strip dispenser of claim 1, wherein the biasing device is located proximal to the guide member.

13. The test strip dispenser of claim 1, wherein the biasing device is located distal to a proximal end of the inner housing.

14. The test strip dispenser of claim 1, further including an anti-jamming mechanism comprised of at least one flipper pivotably attached to an outer surface of the inner housing that engages with a recess on a second inner surface of the outer housing.

15. The test strip dispenser of claim 1, further comprising a spring locator on a proximal end of the guide member.

16. The test strip dispenser of claim 1, further comprising a spring locator on a proximal end of the inner housing.

* * * * *